United States Patent
Brossat et al.

(10) Patent No.: US 11,179,306 B2
(45) Date of Patent: Nov. 23, 2021

(54) USE OF SALICYLIC ACID DERIVATIVES AS PRODESQUAMATING ACTIVE AGENT

(71) Applicant: L'OREAL, Paris (FR)

(72) Inventors: Maude Brossat, Aulnay Sous Bois (FR); Romain Garcon, Aulnay Sous Bois (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 15/107,648

(22) PCT Filed: Dec. 11, 2014

(86) PCT No.: PCT/IB2014/066810
§ 371 (c)(1),
(2) Date: Jun. 23, 2016

(87) PCT Pub. No.: WO2015/097585
PCT Pub. Date: Jul. 2, 2015

(65) Prior Publication Data
US 2016/0331660 A1 Nov. 17, 2016

(30) Foreign Application Priority Data
Dec. 23, 2013 (FR) ...................... 13 63474

(51) Int. Cl.
*A61K 8/368* (2006.01)
*A61Q 19/00* (2006.01)
*C07C 65/05* (2006.01)

(52) U.S. Cl.
CPC .............. *A61K 8/368* (2013.01); *A61Q 19/00* (2013.01); *C07C 65/05* (2013.01); *A61K 2800/28* (2013.01); *A61K 2800/74* (2013.01)

(58) Field of Classification Search
None
See application file for complete search history.

(56) References Cited

U.S. PATENT DOCUMENTS

| 4,767,750 A | 8/1988 | Jacquet et al. |
| 2005/0136015 A1 | 6/2005 | McKie et al. |

FOREIGN PATENT DOCUMENTS

| EP | 0378936 A2 | 7/1990 |
| EP | 0970690 A1 | 1/2000 |
| FR | 2581542 A1 | 11/1986 |
| JP | H06-329516 A | 11/1994 |
| WO | 2006/042391 A2 | 4/2006 |
| WO | 2011/138608 A2 | 11/2011 |

OTHER PUBLICATIONS

Rahman "New Salicylic acid and Isoflavone Derivatives from Flemingia paniculata", 2004, Journal of Natural Products, 67, 402-406.*
Jun. 22, 2015 International Search Report issued in International Patent Application No. PCT/IB2014/066810.
Jun. 22, 2015 Written Opinion issued in International Patent Application No. PCT/IB2014/066810.
Paramashivappa R. et al. "Novel Method for Isolation of Major Phenolic Constituents from Cashew (Anacardium occidentale L.) Nut Shell Liquid." Journal of Agricultural Food Chemistry. 2001, vol. 49, pp. 2548-2551.
Trost, Barry et al. "Regiocontrolled Synthesis of Hydroxyphthalides. Synthesis of (.+-.)-Isoochracinic Acid and a Zealeranone Intermediate." Journal of Organic Chemistry. 1980. vol. 45, pp. 1835-1838.
Pereira, Junia et al. "Anacardic acid derivatives as inhibitors of glyceraldehyde-3-phosphate dehydrogenase from Trypanosoma cruzi." Bioorganic & Medicinal Chemistry, vol. 16, 2008, pp. 8889-8895.
Rodrigues, Francisco et al. "Comparison Between Physico-Chemical Properties of the Technical Cashew Nut Shell Liquid (CNSL) and those Natural Extracted from Solvent and Pressing." Polimeros, vol. 21, No. 2, 2011, pp. 156-160.
Zhang Jingyum, "Practical Cosmetic Pharmacology," China Press of Traditional Chinese Medicine, pp. 133-134, Jul. 31, 2006.
Wang Wei, "Problem Skin Self-Rescue Magic," Hunan Science and Technology Publishing House, p. 46, 2011.

* cited by examiner

*Primary Examiner* — Savitha M Rao
*Assistant Examiner* — Gregg Polansky
(74) *Attorney, Agent, or Firm* — Oliff PLC

(57) ABSTRACT

Cosmetic use of at least one salicylic acid derivative of following formula (I) in which L represents a linear or branched hydrocarbon radical comprising from 1 to 12 carbon atoms and having or not having one or more ethylenic unsaturations, and X represents a radical chosen from —OH and —CO₂H, and also its cosmetically acceptable salts, its solvates, such as its hydrates, and its isomers, in a composition comprising a physiologically acceptable medium, as cosmetic agent intended to promote the desquamation of the skin and/or to stimulate epidermal renewal.

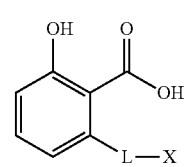

(I)

6 Claims, No Drawings

USE OF SALICYLIC ACID DERIVATIVES AS PRODESQUAMATING ACTIVE AGENT

The invention relates to the use of specific salicylic acid derivatives as agents intended to promote desquamation of the skin and/or to stimulate epidermal renewal.

Desquamation is a natural phenomenon associated with the fact that the epidermis, which constitutes the upper layer of the skin, is constantly being regenerated.

The epidermis is composed of several layers of cells, the deepest of which is the basal layer composed of undifferentiated cells. Over time, these cells will differentiate and migrate towards the surface of the epidermis, making up the various layers thereof, until they form, at the surface of the epidermis, the corneocytes. The stacking of these corneocytes constitutes the horny layer which is responsible for the barrier function of the epidermis. In the course of the normal desquamation process, the most superficial corneocytes detach from the surface of the epidermis. This loss at the surface is compensated for by the migration of cells from the basal layer towards the surface of the epidermis. There is perpetual renewal of the skin.

It is known that the desquamation process can be influenced by exogenous factors (examples: UV radiation, pollution, and the like) and/or endogenous factors (examples: hormonal changes, age, and the like) and can result in particular in a slowing of epidermal renewal and consequently an ageing of the skin and/or a thickening of the horny layer, such as the formation of callosities.

This can also be reflected by a modifying of the appearance of the skin, which may be expressed, for example, by a dry skin, the arrival of squamae, the appearance of a muddy, dull and/or yellow complexion, the appearance of a rough skin and/or the appearance of a "cracked" skin.

Generally, desquamating agents act by facilitating the removal of the dead cells located at the surface of the horny layer of the epidermis.

Mention may in particular be made, among these cosmetic agents promoting desquamation, that is to say the removal of the "dead" cells located at the surface of the horny layer of the epidermis, of α-hydroxy acids (AHAs), such as lactic acid or glycolic acid, or β-hydroxy acids (BHAs), such as salicylic acid. These active agents bring about, by topical application, a desquamation visible after a few days.

Unfortunately, some desquamating compounds can exhibit side effects, such as skin discomfort, indeed even irritation.

As regards salicylic acid, it has in particular been shown that the grafting of a fatty chain, in particular comprising from 3 to 11 carbon atoms, in the 5 position of the salicylic acid makes it possible to enhance its lipophilic nature and thus conferred on it a greater affinity with the first layers of the epidermis. Applications FR 2 581 542 A1 and EP 0 378 936 A2 respectively disclose the use of such compounds for their keratolytic and/or comedolytic effect and for the treatment of ageing of the skin.

However, the abovementioned active agents, when they are applied to skin which is more delicate or rendered sensitive by an external attack, such as cold or wind, and/or at high concentration, can bring about discomfort which can have a limiting effect on their use.

There thus exists a need to find novel prodesquamating compounds which do not have the abovementioned side effects.

In particular, there remains a need to have available novel active agents which are effective when they are employed at reduced concentrations, in comparison with the known active agents, and which exhibit good tolerance and an absence of discomfort on application or after application.

It is a specific object of the present invention to meet this need.

Thus, according to one of its aspects, the invention relates to the cosmetic use of at least one salicylic acid derivative of following formula (I):

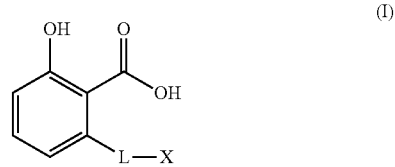

in which:

L represents a linear or branched hydrocarbon radical comprising from 1 to 12 carbon atoms and having or not having one or more ethylenic unsaturations, and X represents a radical chosen from —OH and —CO$_2$H, and also its cosmetically acceptable salts, its solvates, such as its hydrates, and its isomers, in a composition comprising a physiologically acceptable medium, as cosmetic agent intended to promote the desquamation of the skin and/or to stimulate epidermal renewal.

Thus, the present invention is based in particular on the surprising observation that the salicylic acid derivatives of formula (I) as defined above prove to be very particularly useful in improving the appearance and/or the texture of the skin. Advantageously and as demonstrated in the examples below, these derivatives exhibit desquamating properties associated with good tolerance, preserving the morphology of the epidermis, without bringing about discomfort on application and/or after application.

Thus, the present invention relates to the cosmetic use of at least one salicylic acid derivative of formula (I) or one of its salts and/or solvates and/or isomers in a composition intended to combat imperfections of the skin, to render uniform the relief of the skin, to render uniform the complexion, to close the pores, to remove bumps by providing a smoothing-out effect, to reduce surface irregularities and the skin microrelief, to improve the radiance of the complexion and/or to improve the wear property of the make-up and/or to promote the cleaning action and the removal of dead cells at the surface of the body or face.

According to another of its aspects, the present invention relates to a cosmetic treatment method employing a composition comprising at least one salicylic acid derivative of formula (I) or one of its salts and/or solvates and/or isomers, which composition is intended to combat imperfections of the skin, to render uniform the relief of the skin, to render uniform the complexion, to close the pores, to remove bumps by providing a smoothing-out effect, to reduce surface irregularities and the skin microrelief, to improve the radiance of the complexion and/or to improve the wear property of the make-up.

It is also targeted at a cosmetic treatment method for promoting the radiance of the complexion and/or decreasing the surface irregularities of the skin and/or mucous membranes, characterized in that at least one salicylic acid derivative of formula (I) or one of its salts and/or solvates and/or isomers, or a composition comprising it/them, is applied to the skin or mucous membranes.

For the implementation of these methods, the salicylic acid derivative of formula (I) or one of its salts and/or solvates and/or isomers, or the composition comprising it, can be applied to any region of the skin, in particular of the face, neck and shoulders, or hands, or to the lips, in order to tone down the visible and/or tactile irregularities of the skin, for example in order to tone down scars, to smooth out the surface and/or to remove dead skin, in particular from the lips.

Admittedly, some of the derivatives of formula (I) are already described in the prior art. However, to the knowledge of the inventors, they have never been employed for the purposes of the present invention.

For example, the document Junia M. Pereira et al., *Biorganic & Medicinal Chemistry*, 16 (2008), 8889-8895, discloses the compound A of following formula for pharmaceutical purposes as inhibitor of glyceraldhehyde 3-phosphate dehydrogenase originating from *Trypanosoma cruzi*.

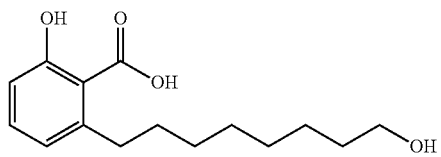

A

The document WO 2006/042391 for its part provides for the use of compounds according to the invention but for UV-absorbing purposes.

Consequently, to the knowledge of the inventors, the salicylic acid derivatives of general formula (I) and their salts and/or solvates and/or isomers are for the first time characterized for their desquamating properties.

According to another of its aspects, the present invention relates to some derivatives of formula (I) as such and to the compositions, in particular cosmetic compositions, comprising them.

More specifically, these novel compounds are the compounds of general formula (Ia), the compound C, the compounds of general formula (Ib), the compounds of general formula (Ic) and/or the compounds of general formula (Id) or one of their salts, solvates or isomers as described in detail below. The invention also relates to a composition, in particular a cosmetic composition, comprising, in a physiologically acceptable medium, at least one salicylic acid derivative chosen from a compound of general formula (Ia), the compound C, a compound of general formula (Ib), a compound of general formula (Ic) and/or a compound of general formula (Id) as defined below or one of their salts, solvates or isomers. According to a preferred alternative form, such a composition comprises at least the compound B as defined below or one of its salts and/or solvates.

Other characteristics and advantages of the invention will become more clearly apparent on reading the description which will follow, given by way of illustration and without implied limitation.

In the continuation of the text, the expressions "of between . . . and . . . ", "ranging from . . . to . . . " and "varying from . . . to . . . " are equivalent and are intended to mean that the limits are included, unless otherwise indicated.

Unless otherwise indicated, the expression "comprising a" should be understood as "comprising at least one".

Salicylic Acid Derivatives According to the Invention

As mentioned above, the invention is based on the cosmetic use of at least one salicylic acid derivative of following formula (I):

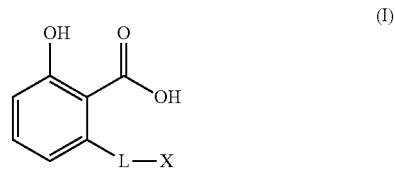

(I)

in which:
L represents a linear or branched hydrocarbon radical comprising from 1 to 12 carbon atoms and having or not having one or more ethylenic unsaturations, and
X represents a radical chosen from —OH and —CO$_2$H,
and also its cosmetically acceptable salts and/or its solvates, such as the hydrates, and/or its isomers.

According to one embodiment of the invention, it is also possible to use a salicylic acid derivative of natural or renewable origin.

Compound "of natural origin" is understood to mean a natural compound which has been subjected to one or more additional chemical or industrial treatments bringing about modifications which may be structural modifications resulting in other compounds.

The cosmetically acceptable salts of the salicylic acid derivatives of formula (I) according to the present invention comprise conventional non-toxic salts of the said compounds.

Within the meaning of the present invention, the terms cosmetically acceptable and physiologically acceptable are equivalent.

Cosmetically acceptable salt is intended to denote any salt suitable for the topical administration of a composition comprising it.

A cosmetically acceptable salt is preferably a cosmetically or dermatologically acceptable salt, that is to say a salt which is devoid of unpleasant odour or appearance and which is entirely compatible with the topical administration route. In the present case, where the composition is intended to be administered topically, that is to say by application at the surface of the keratinous substance under consideration, such a compound is in particular considered as physiologically acceptable when it does not cause stinging, tightness or redness unacceptable to the user.

These salts can be organic or inorganic.

Mention may in particular be made, among inorganic salts, of alkali metal salts, such as sodium or potassium salts, alkaline earth metals salts, such as calcium, strontium or magnesium salts, or also transition metal salts, such as copper, iron or manganese salts.

Mention may be made, among organic salts, of amines in their cationic form, that is to say primary, secondary or tertiary ammoniums, and also quaternary ammoniums. In particular, the cationic form of triethanolamine, monoethanolamine, diethanolamine, hexadecylamine, N,N,N',N'-tetrakis(2-hydroxypropyl)ethylenediamine or tris(hydroxymethyl)aminomethane may be concerned.

According to a specific form of the invention, the salt is the cationic form of an amino acid of L or D form, such as, for example, the cationic form of lysine, arginine, alanine or tryptophan, or else a quaternary ammonium of following formula (IV):

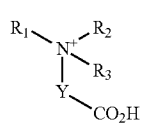

in which:

R₁, R₂ and R₃, which are identical or different, denote a saturated linear hydrocarbon radical comprising from 1 to 12 carbon atoms, and Y denotes a saturated linear hydrocarbon radical comprising from 2 to 6 carbon atoms.

The acceptable solvates for the salicylic acid derivatives of formula (I) according to the present invention comprise conventional solvates, such as those formed during the final stage of preparation of the said compounds due to the presence of solvents. Mention may be made, by way of example, of the solvates due to the presence of water or of linear or branched alcohols, such as ethanol or isopropanol.

The term "isomer" is to be understood within the meaning of the invention as optical isomer and/or as geometrical isomer (cis/trans isomerism of ethylenic unsaturations); it encompasses mixtures of optical isomers, in particular the racemic mixture.

In the context of the present invention, "hydrocarbon radical" is understood to mean an aliphatic radical composed of carbon atoms and of hydrogen atoms. Unless otherwise indicated, such a radical can comprise from 1 to 12 carbon atoms, can be linear or branched and may or may not have one or more ethylenic unsaturations.

A hydrocarbon radical according to the invention can be monovalent or divalent. A hydrocarbon radical is said to be "divalent" when it is bonded to two other entities. A hydrocarbon radical is said to be "monovalent" when it is bonded to just one other entity.

According to one embodiment of the invention, use may be made of a salicylic acid derivative of formula (I) or one of its salts and/or solvates and/or isomers in which L represents a linear or branched hydrocarbon radical comprising from 6 to 10 carbon atoms and having or not having one or more ethylenic unsaturations.

Preferably, L represents a saturated linear hydrocarbon radical comprising from 6 to 10 carbon atoms. In particular, L represents a heptylene or octylene radical.

More particularly, when L represents a heptylene radical, X can advantageously represent the —CO₂H radical, in order to form the following compound B or one of its salts and/or solvates:

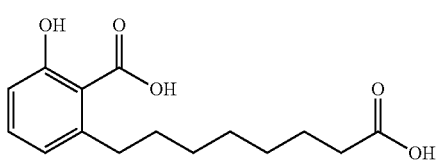

More particularly, when L represents an octylene radical, X can advantageously represent the —OH radical, in order to form the following compound A or one of its salts and/or solvates:

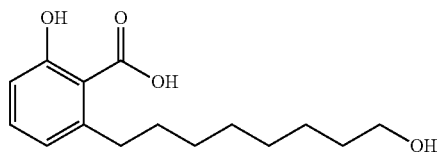

Thus, the salicylic acid derivative of formula (I) is advantageously chosen from the abovementioned compounds A and B, and also from their salts and/or solvates.

Of course, according to the invention, a salicylic acid derivative corresponding to the formula (I) or one of its salts and/or solvates and/or isomers can be used alone or as a mixture with other derivatives of formula (I) or one of their salts and/or solvates and/or isomers and in all proportions.

As specified above, some of the derivatives of formula (I) are novel.

Consequently, the present invention is also targeted at these compounds as such.

Thus, according to one of its aspects, the present invention relates to a compound chosen from:

a compound of following formula (Ia):

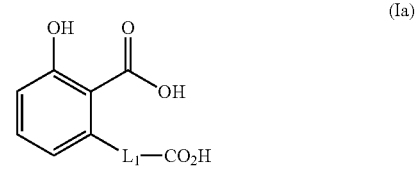

in which:

L₁ represents a linear or branched hydrocarbon radical comprising from 3 to 12 carbon atoms and having or not having one or more ethylenic unsaturations, and also its cosmetically acceptable salts, its solvates, such as the hydrates, and its isomers, and the following compound C:

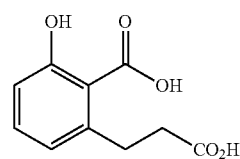

and also the cosmetically acceptable salts and/or the solvates, such as the hydrates, of the compounds C.

In particular, a compound of formula (Ia) can advantageously be the compound of following formula B:

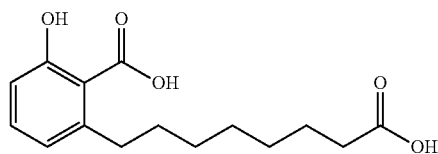

and also its cosmetically acceptable salts and/or its solvates, such as the hydrates.

The present invention is also targeted at a compound of following formula (Ib):

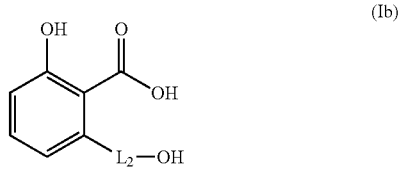

in which:

$L_2$ represents a linear or branched hydrocarbon radical comprising from 2 to 12 carbon atoms and having one or more ethylenic unsaturations, and also its cosmetically acceptable salts, its solvates, such as the hydrates, and its isomers.

Another subject-matter of the invention relates to a compound of following formula (Ic):

(Ic)

in which n is an integer chosen from 2, 3, 4, 5, 7, 9, 11 and 12, and also its cosmetically acceptable salts, its solvates, such as the hydrates, and its isomers.

According to another of its aspects, the present invention also relates to a compound of following formula (Id):

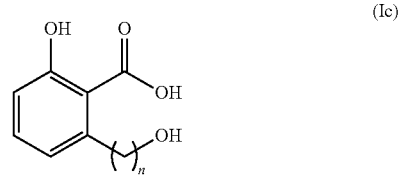

in which:

$L_3$ represents a saturated branched hydrocarbon radical comprising from 3 to 12 carbon atoms, and also its cosmetically acceptable salts, its solvates, such as the hydrates, and its isomers.

Thus, the invention also relates to a composition, in particular a cosmetic composition, comprising, in a physiologically acceptable medium, at least one salicylic acid derivative chosen from a compound of general formula (Ia), the compound C, a compound of general formula (Ib), a compound of general formula (Ic), a compound of general formula (Id) as are defined above, one of its salts and/or solvates and/or isomers, and their mixtures. According to a preferred alternative form, such a composition is a cosmetic composition and comprises at least the compound B as defined above.

Preparation of the Salicylic Acid Derivatives According to the Invention

The salicylic acid derivatives of formula (I) and in particular the compounds A and B, as well as the salicylic acid derivatives of formulae (Ia), (Ib), (Ic) and (Id) and the compound C, according to the invention, can be prepared according to different methods, illustrated in the following schemes, according to which X denotes an —OH radical or a —CO$_2$H radical.

The implementation of each of these stages clearly ensues from the abilities of a person skilled in the art.

Thus, the compounds of formula (I) for which X=CO$_2$H, in particular the novel compounds (Ia) and the compound C, can be prepared according to the following Scheme 1:

Scheme 1

More specifically, the compounds of formula (I) can thus be obtained from the compounds 1c (x=1 to 12). The reaction of 3-fluoroanisole 1a with 1c in the presence of lithium results in the compound 2b. The treatment of 2b with carbon dioxide, the acid hydrolysis and then the treatment with diazomethane makes it possible to obtain the compound 3b. The transformation of the alcohol 3b into carboxylic acid can be carried out by bromination in the presence of PBr$_3$, followed by treatment with potassium cyanide. Finally, the compound (I) with X=CO$_2$H can be obtained by reaction with BBr$_3$ in dichloromethane, for example, followed by the treatment with sodium hydroxide in a protic solvent, such as ethanol.

The compounds of formula (I) for which X=OH, in particular the novel compounds having the structures (Ib), (Ic) and (Id), can be obtained according to Scheme 2.

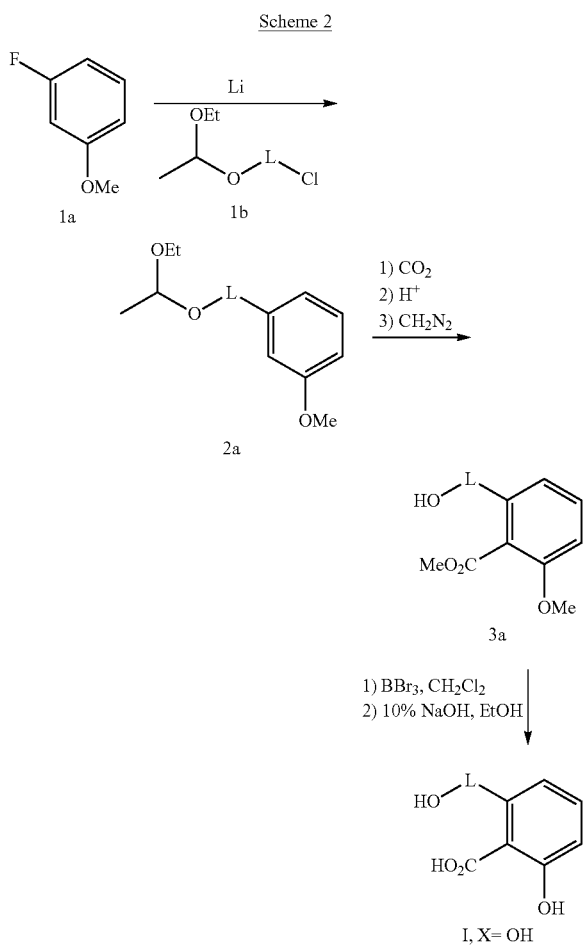

In particular, these compounds of formula (I) for which X=OH can be obtained from the compounds 1b (L having the same meaning as above). The reaction of 3-fluoroanisole 1a with 1b in the presence of lithium results in the compound 2a. The treatment of 2a with carbon dioxide, then the acid hydrolysis and the treatment with diazomethane makes it possible to obtain the compound 3a. The reaction of 3a with BBr$_3$ in dichloromethane, for example, followed by the treatment with sodium hydroxide in a protic solvent, such as ethanol, results in the compound (I) for which X=OH.

Furthermore, the compounds A and B having the following formulae can also be obtained according to another method starting from a natural starting material extracted from the cashew nut shell:

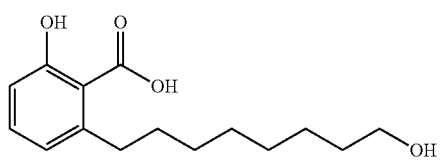

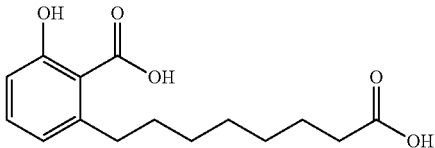

The compound A can be obtained by employing the process described in Patent WO2011138608 (Bangor University). In this process, the reduction stage can be carried out with zinc or by catalytic hydrogenation with Pd/C.

The synthesis of compound A is also described in Bioorg. & Med. Chem., 2008, 8889-8895, and J. Braz. Chem. Soc., 2005, 16, 1217-1225.

As regards the preparation of the compound B, a first stage consists of the preparation of the "raw" or "natural" liquid extracted from the cashew nut (*Anacardium occidentale*) shell (CNSL) (Cashew Nut Shell Liquid) comprising from 60% to 80% of anacardic acids, according to the methods described in Polimeros, 2011, 21, 156-160.

In a second stage, the mixture of anacardic acids is isolated from the "natural" CNSL, for example according to the method described in J. Agric. Food Chem., 2001, 49, 2548-2551, and illustrated by the following Scheme 3.

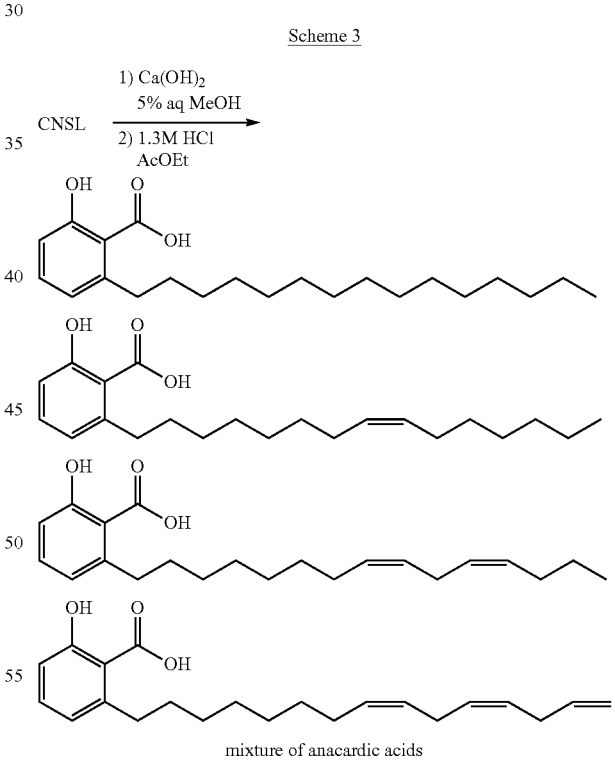

mixture of anacardic acids

In a third stage, the compound B can be obtained from the mixture of the anacardic acids by ozonolysis, followed by cleavage of the ozonide by a reducing treatment with sodium borohydride or by catalytic hydrogenation with Pd/C or NaBH$_4$ and oxidation of the aldehyde generated in the presence of molecular oxygen. The latter stage is described in detail in the following Example 2.

Cosmetic Compositions and Uses According to the Invention

As emerges from the above, the salicylic acid derivatives of formula (I) and in particular the compounds A and B, as well as the salicylic acid derivatives of formulae (Ia), (Ib), (Ic) and (Id) and the compound C, according to the invention, and also their cosmetically acceptable salts, their solvates, such as their hydrates, and their isomers, are employed in the context of the present invention for in particular their desquamating properties.

For these purposes, they are advantageously formulated in compositions in particular having a cosmetic use.

The amount of salicylic acid derivative of formula (I), having the formulae (Ia), (Ib), (Ic) and (Id), and in particular of compound(s) A, B and/or C to be considered in a composition or use according to the invention depends on the cosmetic effect desired and can thus vary to a large extent.

A person skilled in the art can, on the basis of his general knowledge, readily determine the appropriate amounts.

By way of indication, one or more salicylic acid derivatives corresponding to the formula (I), (Ia), (Ib), (Ic) or (Id) or the compound C or one of their salts and/or isomers and/or solvates can be employed in a composition at a content ranging from 0.01% to 20% by weight, better still from 0.01% to 10% by weight and in particular from 0.1% to 5% by weight of derivative(s), with respect to the total weight of the composition.

Generally, a salicylic acid derivative of formula (I), (Ia), (Ib), (Ic) or (Id) or the compound C or one of its salts and/or isomers and/or solvates can be used in topical mode at a concentration ranging from 0.01% to 20% by weight, better still from 0.01% to 10% by weight, and preferably of between 0.1% and 5% by weight of active material, with respect to the total weight of the composition.

This or these salicylic acid derivatives according to the invention are formulated in compositions comprising a physiologically acceptable medium, that is to say a medium compatible with all keratinous substances and in particular the skin.

Thus, a composition according to the invention can comprise an aqueous phase. It can be an aqueous or aqueous/alcoholic medium formed or not of a mixture with one or more organic solvents, such as a $C_1$-$C_8$ alcohol, in particular ethanol, isopropanol, tert-butanol or n-butanol, polyols, such as glycerol, propylene glycol or butylene glycol, and polyol ethers.

A composition according to the invention can also be anhydrous.

A composition according to the invention can also be an emulsion. The proportion of the fatty phase can then vary from 5% to 80% by weight and preferably from 5% to 50% by weight, with respect to the total weight of the composition.

This fatty phase can also comprise, in addition to oils, gums or waxes normally used in the field of application under consideration.

Mention may be made, as oils or waxes which can be used in the invention, of mineral oils (liquid petrolatum), vegetable oils (liquid fraction of shea butter, sunflower oil, apricot oil, rice bran oil, and the like), animal oils (perhydrosqualene), synthetic oils (purcellin oil), silicone oils or waxes (cyclomethicone, dimethicone), fluorinated oils (perfluoropolyethers), beeswax, carnauba wax, paraffin wax, shea butter or hydrogenated jojoba oil. Fatty alcohols (cetyl, stearyl, and the like) and fatty acids (stearic acid, and the like) can be added to these oils.

Consequently, the compositions under consideration according to the invention can be provided in any formulation form normally used in cosmetics. Thus, they can be provided in the form of aqueous, aqueous/alcoholic or oily solutions, of dispersions of the lotion or serum type, of anhydrous or oily gels, of emulsions with a liquid or semi-liquid consistency of the milk type, obtained by dispersion of a fatty phase in an aqueous phase (O/W) or vice versa (W/O), of suspensions or emulsions with a soft, semi-solid or solid consistency of the cream or gel type, of microemulsions or also of microcapsules, microparticles or vesicular dispersions of ionic and/or non-ionic type. These compositions are prepared according to the usual methods.

Preferably, a composition according to the invention is an aqueous composition.

A composition according to the invention can additionally comprise adjuvants normal in the cosmetics field, such as hydrophilic or lipophilic gelling agents, thickeners, preservatives, antioxidants, solvents, fragrances, fillers, screening agents, pigments, odour absorbers, pH agents and colourants.

Mention may in particular be made, as hydrophilic gelling agents, of carboxyvinyl polymers (carbomer), acrylic copolymers, such as acrylate/alkyl acrylate copolymers, polyacrylamides, polysaccharides, clays and natural gums and mention may be made, as lipophilic gelling agents, of modified clays, such as bentones, metal salts of fatty acids, hydrophobic silica and polyethylenes.

The amounts of these various adjuvants are those conventionally used in the field under consideration, for example from 0.01% to 20% of the total weight of the composition.

Depending on their nature, these adjuvants may be introduced into the fatty phase or into the aqueous phase. In any case, these adjuvants and their proportions will be chosen so as not to harm the desired properties of the salicylic acid derivatives according to the invention.

The compositions according to the invention can advantageously constitute in particular protection, treatment or care creams for the face, for the hands or for the body, or protection or care body milks, or lotions, gels or foams for the care of the skin and mucous membranes or for cleansing the skin, or masks or also patches.

They can also consist of solid preparations constituting soaps or cleansing bars.

The compositions which can be used according to the invention can also be packaged in the form of an aerosol composition also comprising a pressurized propellant.

Compositions according to the invention can thus advantageously be compositions intended for cleansing the skin of the face or body, in which the action of the cleansing agents will be reinforced by promoting the removal of the dead cells from the cleansed surface.

The salicylic acid derivatives of formula (I), (Ia), (Ib), (Ic) or (Id) or the compound C or one of its salts and/or isomers and/or solvates according to the invention are thus particularly advantageous in a care composition intended to improve the surface condition of the skin and/or mucous membranes, in particular of the lips. A composition comprising at least one salicylic acid derivative of formula (I), (Ia), (Ib), (Ic) or (Id) or the compound C or one of its salts and/or isomers and/or solvates according to the invention is also particularly effective in removing the roughnesses and/or dead skin present at the surface of the skin and/or lips.

The compositions according to the invention can in particular be exfoliating compositions suitable for the scrubbing of the roughnesses of the skin. They can also be peeling compositions which make it possible to remove a greater thickness of horny layer, such as calluses.

The compositions comprising at least one salicylic acid derivative of formula (I), (Ia), (Ib), (Ic) or (Id) or the compound C or one of its salts and/or isomers and/or solvates according to the invention are thus more particularly dedicated to being applied to the face, neck, mucous membranes or any other cutaneous region of the body.

The application times will vary as a function of the nature of the formulation under consideration, of the concentration of salicylic acid derivative according to the invention in the composition and of the effect desired.

By way of indication, a composition can remain in contact with the skin for between 1 min and 12 h; it may or may not be removed on conclusion of this contact time. Application may be daily or twice daily, or weekly, and be repeated for periods of 1 week to 6 months, it being possible for this period to be extended or renewed without difficulty.

The invention is illustrated in more detail in the following examples. These examples cannot in any way limit the scope of the invention.

EXAMPLES

Example 1

Synthesis of the Compound A

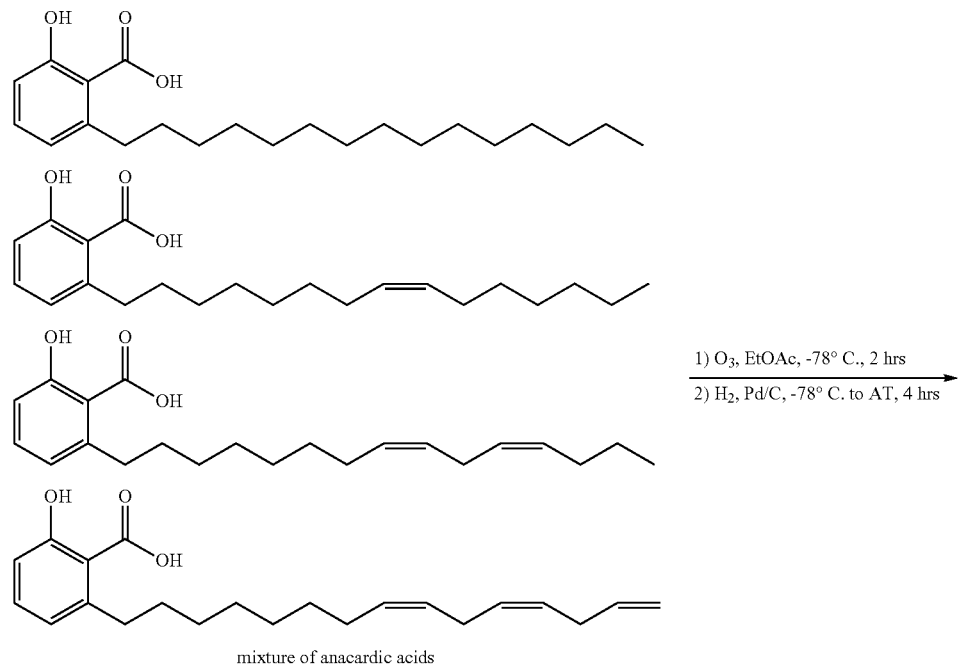

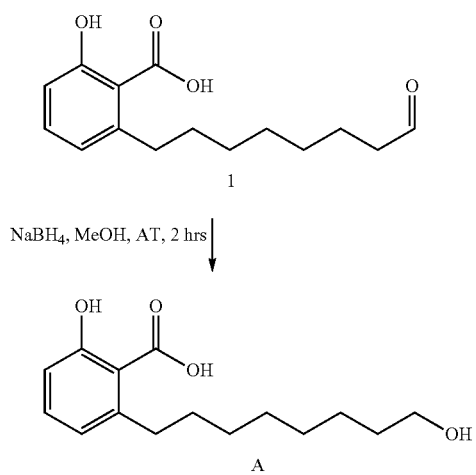

2 g of mixture of anacardic acids prepared according to the method described in *J. Agric. Food Chem.*, 2001, 49, 2548-2551, are ozonolysed in 50 ml of ethyl acetate at −78° C. for 2 hours. The reaction is monitored by thin layer chromatography until the anacardic acid has disappeared. After evaporation of the solvent, the mixture obtained is hydrogenated in the presence of 5% palladium-on-charcoal (0.24 g) in 50 ml of ethanol for 4 hours. The catalyst is filtered off through Celite and the filtrate is evaporated under reduced pressure. Purification by chromatography on silica gel (petroleum ether/ethyl acetate with ratios by volume from 20/1 to 5/1) makes it possible to obtain the intermediate aldehyde 1 (0.7 g). This intermediate is subsequently reduced by using 1.5 equivalents (100 mg) of sodium borohydride in 100 ml of methanol at ambient temperature for 2 hours in order to result, after washing operations with a 0.1M hydrochloric acid solution, extraction with 2*100 ml of ethyl acetate and evaporation of the solvent under reduced pressure, in 0.42 g of the compound A in the form of a white solid.

The NMR spectrum and the elemental analysis confirm the structure of the expected compound.

Example 2

Synthesis of the Compound B

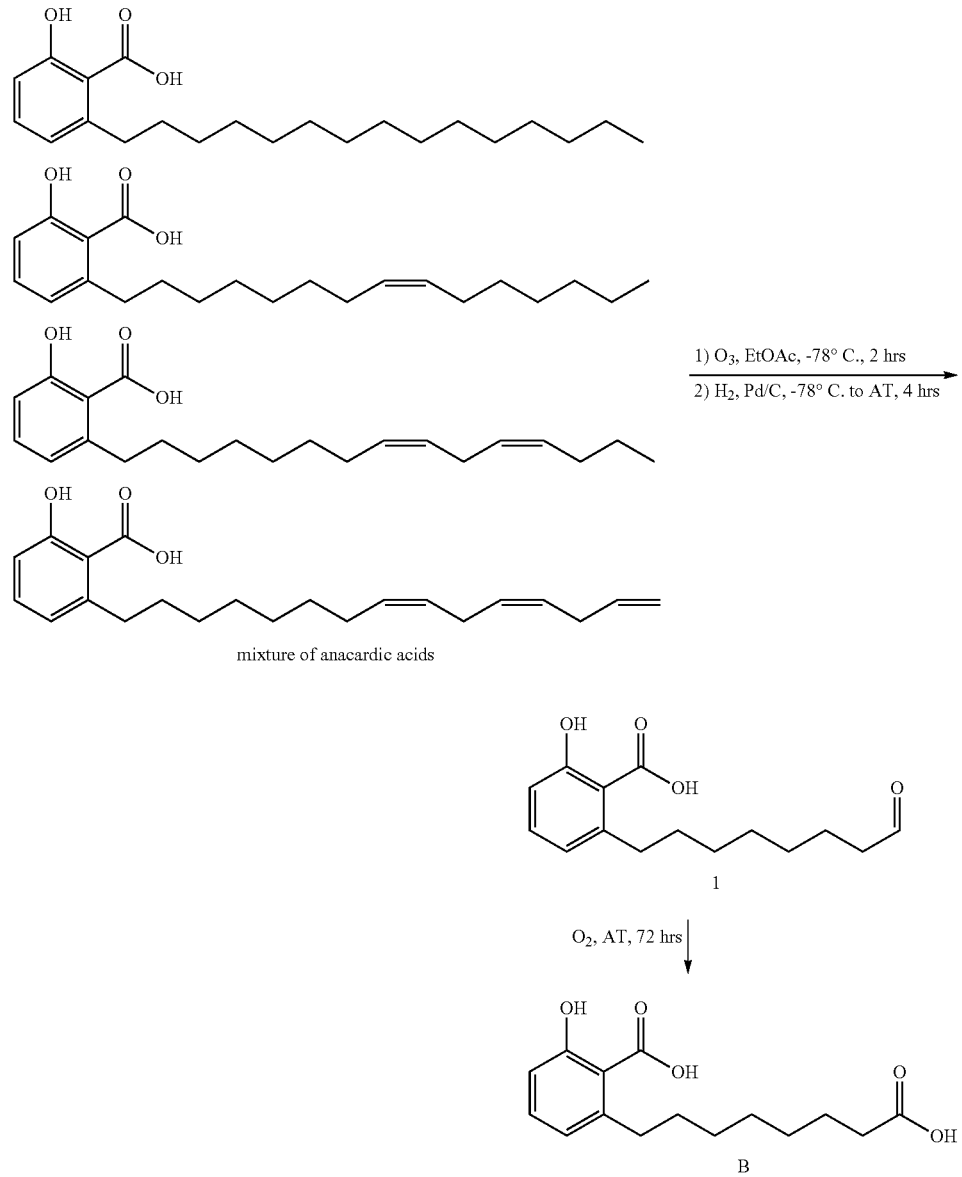

2 g of mixture of anacardic acids prepared according to the method described in *J. Agric. Food Chem.*, 2001, 49, 2548-2551, are ozonolysed in 50 ml of ethyl acetate at −78° C. for 2 hours. The reaction is monitored by thin layer chromatography until the anacardic acid has disappeared. After evaporation of the solvent, the mixture obtained is hydrogenated in the presence of 5% palladium-on-charcoal (0.24 g) in 50 ml of ethanol for 4 hours. The catalyst is filtered off through Celite and the filtrate is stirred in the air for 72 hours. The medium is then evaporated under reduced pressure and the residue is purified by chromatography on silica gel (petroleum ether/ethyl acetate with ratios by volume from 20/1 to 5/1) in order to result in 0.42 g of the compound B in the form of a white solid.

The NMR spectrum and the elemental analysis confirm the structure of the expected compound.

Example 3

Evaluation of the Desquamating Activity of the Compounds A and B

The study is targeted at detecting the desquamating potential of the active agents in simplex solution by observation of the cohesion of the stratum corneum.

The keratolytic effect on excised skin maintained under survival conditions at 5% by weight in ethanol was evaluated. The study was carried out on viable human skin resulting from abdominal or breast reduction plastic surgery (6 donors).

The protocol consists in applying the test solutions to skin samples maintained under survival conditions. The products tested are applied in a proportion of 15 µl per 1 cm² sample and are not rinsed off. Application is carried out twice, at D0 and then, 24 hours later, at D1. The morphology of the stratum corneum is analysed 48 hours after the first application, at D2, on a biopsy.

The solutions applied are the following:
compound A of Example 1, at 5% by weight in ethanol, and
compound B of Example 2, at 5% by weight in ethanol.

By way of comparison, no solution is applied to some samples, referred to as controls.

The histological analysis of the horny layer is carried out on a skin section after staining with hemalaun-eosin (magnification 400). The decrease in the cohesion of the stratum corneum is expressed in the form of a score:
score 0: absence of modification
score 1: slight decrease
score 2: moderate decrease
score 3: large decrease
score 4: very large decrease with exfoliation The results obtained appear in the following table. 6 samples were used for each of the tests (control, compound A and compound B). A paired Student test (p<0.05) was carried out in order to evaluate the significance of the difference with respect to the control.

| Product | Score (mean ± sd, n = 6) | Statistic |
|---|---|---|
| None (control) | 1.20 ± 0.2 | / |
| EtOH | 0.98 ± 0.4 | / |
| Compound A at 5% in EtOH | 1.85 ± 0.4 | *p = 0.008 |
| Compound B at 5% in EtOH | 1.75 ± 0.2 | *p = 0.01 |

*p: significant difference with respect to the untreated skin control (paired Student, p < 0.05)

Thus, the compounds A and B at 5% really do bring about a decrease in the cohesion of the stratum corneum. This decrease is statistically significant with respect to the control skin and illustrates a desquamating effect at this concentration.

In order to validate the desquamating properties of the compounds A and B and to evaluate the tolerance of the skin to these treatments, the morphology of a control skin was in addition compared with the morphology of the skin samples treated with A and with B present in a content of 5% by weight in ethanol, according to the protocol described above.

The appearance of the stratum corneum was studied in order to evaluate the desquamating properties of A and B and the morphology of the epidermis was observed in order to determine the tolerance of the skin with respect to these compounds.

A decrease in the cohesion of the stratum corneum and also the preservation of the morphology of the epidermis were observed, which clearly illustrates the desquamating property of the compounds A and B in combination with good tolerance of the skin.

Example 4

Composition Examples

The three compositions which follow for topical application to the face are prepared.

| Composition 1: | |
|---|---|
| Components | Amount as percentage by weight |
| Carbomer | 0.3 |
| Preservatives | q.s. |
| Compound A | 0.1 |
| Water | q.s. for 100 |

| Composition 2: | |
|---|---|
| Components | Amount as percentage by weight |
| Carbomer | 0.3 |
| Preservatives | q.s. |
| Compound B | 1 |
| Water | q.s. for 100 |

| Composition 3: | |
|---|---|
| Components | Amount as percentage by weight |
| Carbomer | 0.3 |
| Preservatives | q.s. |
| Compound B | 5 |
| Water | q.s. for 100 |

These compositions can be applied to the face daily or at the rate of once weekly, according to the effect desired.

The invention claimed is:
1. Cosmetic method comprising:
identifying an individual in need of promotion of desquamation of the skin and/or stimulation of epidermal renewal due to influence of exogenous factors and/or endogenous factors, with the exclusion of UV radiation,
applying to the individual's skin, as cosmetic agent, at least one salicylic acid derivative of following formula (I):

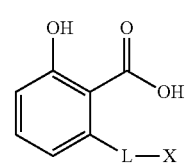

in which:
L represents a saturated linear hydrocarbon radical comprising from 6 to 10 carbon atoms composed of carbon atoms and of hydrogen atoms, and
X represents a radical chosen from —OH and —CO$_2$H, or a salt, solvate, or isomer thereof, or a composition comprising the salicylic acid derivative of formula (I) or a salt, solvate, isomer, or mixture thereof, and promoting the desquamation of the skin and/or stimulating epidermal renewal.

2. Cosmetic method comprising:
identifying an individual in need of improving the appearance and/or the texture of the skin due to influence of exogenous factors and/or endogenous factors, with the exclusion of UV radiation,
applying to the individual's skin, as cosmetic agent, at least one salicylic acid derivative of following formula (I):

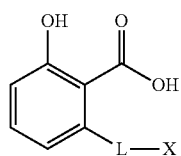
(I)

in which:
L represents a saturated linear hydrocarbon radical comprising from 6 to 10 carbon atoms composed of carbon atoms and of hydrogen atoms, and
X represents a radical chosen from —OH and —CO$_2$H, or a salt, solvate, or isomer thereof, or a composition comprising the salicylic acid derivative of formula (I) or a salt, solvate, isomer, or mixture thereof, and improving the appearance and/or the texture of the skin.

3. Cosmetic method comprising:
identifying an individual in need of at least one of combating imperfections of the skin, rendering uniform the relief of the skin, rendering uniform the complexion, closing the pores, removing bumps by providing a smoothing-out effect, reducing surface irregularities and the skin microrelief, improving the radiance of the complexion, improving the wear property of the make-up, and promoting the cleaning action and the removal of dead cells at the surface of the body or face due to influence of exogenous factors and/or endogenous factors, with the exclusion of UV radiation,
applying to the individual's skin, as cosmetic agent, at least one salicylic acid derivative of following formula (I):

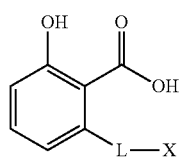
(I)

in which:
L represents a saturated linear hydrocarbon radical comprising from 6 to 10 carbon atoms composed of carbon atoms and of hydrogen atoms, and X represents a radical chosen from —OH and —CO$_2$H, or a salt, solvate, or isomer thereof, or a composition comprising the salicylic acid derivative of formula (I) or a salt, solvate, isomer, or mixture thereof, and combating imperfections of the skin, rendering uniform the relief of the skin, rendering uniform the complexion, closing the pores, removing bumps by providing a smoothing-out effect, reducing surface irregularities and the skin microrelief, improving the radiance of the complexion, improving the wear property of the make-up, and promoting the cleaning action and the removal of dead cells at the surface of the body or face.

4. Method according to claim 1, wherein said salicylic acid derivative is of natural or renewable origin.

5. Method according to claim 1, wherein said salicylic acid derivative is chosen from the following compounds A and B, their salts and/or solvates:

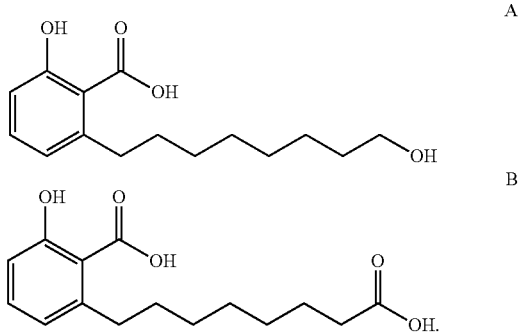

6. Cosmetic treatment method comprising:
identifying an individual in need of promoting the radiance of the complexion and/or decreasing the surface irregularities of the skin and/or mucous membranes due to influence of exogenous factors and/or endogenous factors, with the exclusion of UV radiation,
applying to the individual's skin or mucous membranes at least one salicylic acid derivative of formula (I)

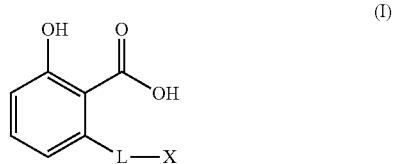
(I)

in which:
L represents a saturated linear hydrocarbon radical comprising from 6 to 10 carbon atoms composed of carbon atoms and of hydrogen atoms, and
X represents a radical chosen from —OH and —CO$_2$H, or a salt, solvate, or isomer thereof, or a composition comprising the salicylic acid derivative of formula (I) or a salt, solvate, isomer, or mixture thereof, and promoting the radiance of the complexion and/or decreasing the surface irregularities of the skin and/or mucous membranes.

* * * * *